(12) United States Patent
Bingham

(10) Patent No.: US 8,615,411 B2
(45) Date of Patent: *Dec. 24, 2013

(54) SYSTEM AND METHOD FOR VERIFYING MEDICAL IMPAIRMENTS

(76) Inventor: Christopher Roy Bingham, Kailua, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/478,022

(22) Filed: May 22, 2012

(65) Prior Publication Data

US 2012/0232924 A1 Sep. 13, 2012

Related U.S. Application Data

(63) Continuation of application No. 12/409,393, filed on Mar. 23, 2009, now Pat. No. 8,185,410.

(51) Int. Cl.
*G06Q 10/00* (2012.01)
*G06Q 50/00* (2012.01)

(52) U.S. Cl.
USPC .......................................................... 705/2

(58) Field of Classification Search
USPC ....................................................... 705/2, 3
See application file for complete search history.

(56) References Cited

U.S. PATENT DOCUMENTS

| 7,337,121 | B1 * | 2/2008 | Beinat et al. ...................... 705/3 |
| 2007/0250352 | A1 * | 10/2007 | Tawil ................................ 705/4 |
| 2008/0154672 | A1 * | 6/2008 | Skedsvold ........................ 705/7 |
| 2011/0182820 | A1 * | 7/2011 | Seeburger et al. ............. 424/9.2 |

OTHER PUBLICATIONS

Differences in workers' compensation ratings. Department of Public Health Sciences Univ. of California, Davis, CA; Date: Jul. 5. 2005: revision Sep. 2, 2005.

* cited by examiner

*Primary Examiner* — John Pauls
*Assistant Examiner* — Trang Nguyen
(74) *Attorney, Agent, or Firm* — Sheppard Mullin Richter & Hampton LLP

(57) ABSTRACT

The present invention provides a method of verifying a medical impairment, comprising receiving a medical diagnosis of an injury, the numeric permanent impairment rating resulting from an evaluation of a permanent impairment, and comparing that permanent impairment rating to a statistically evaluated probable impairment rating of the injury. Depending on the results of the comparison, the assessed impairment rating may be reevaluated, in some cases by a trained impairment evaluator, and others by an expert medical staff.

17 Claims, 7 Drawing Sheets

SYSTEM AND METHOD FOR VERIFYING MEDICAL IMPAIRMENTS

REFERENCE TO RELATED APPLICATIONS

This application is a continuation of U.S. patent application Ser. No. 12/409,393, filed on Mar. 23, 2009, the content of which is incorporated herein by reference in its entirety.

TECHNICAL FIELD

The present invention relates to medical impairments, and more particularly, some embodiments relate to medical permanent impairment verification.

DESCRIPTION OF THE RELATED ART

The efficient allocation of resources can be increased by an objective system of evaluating the impacts of medical injuries and illnesses. Increased objectivity allows a resource allocator to better trust, and depend on, the validity and reliability of permanent impairment evaluations received from different evaluators. The American Medical Association publishes the *AMA Guides to the Evaluation of Permanent Impairment* (the *Guides*) to serve this need for objectivity. The *Guides* defines impairment as "a loss, loss of use, or derangement of any body part, organ system, or organ function." (*Guides*, p. 2, $5^{th}$ ed.) An impairment is considered permanent when it has reached its maximum medical improvement (MMI). (Id.) The *Guides* measures impairment in impairment percentages or ratings on a whole person (VIP) scale where 0% WP indicates an impairment that has no effect on daily living and where 100% WP indicates a completely debilitating impairment.

The impairment ratings based on the Guides are the most commonly used. They are used in over 40 state workers' compensation jurisdictions in the United States and are estimated to drive twenty billion dollars of cost per year. They also frequently used in personal injury cases, cases involving the government, and internationally.

Despite the procedures defined in the *Guides*, the majority of impairment ratings are performed erroneously because the procedures are not consistently followed. Studies have demonstrated that it is twenty times more likely for a rating to be too high than too low, and that the average incorrect rating is almost three times higher than the appropriate rating.

Sources of this inconsistency include the complexity of the *Guides* prevents professionals from reliably defining impairment. This is compounded by multiple circulating editions of the resource, the most common being the Forth, Fifth, and Sixth editions, each varying in their approaches to some impairment definitions. Furthermore, data on physician performance is not captured and therefore it is difficult to identify reliable physicians.

Because of the availability of inconsistent ratings, the parties with a stake in the resource allocation, for example a claimant and an insurer will often disagree on the proper impairment rating value, resulting in conflicts and delays in case resolution. Furthermore, the difficulty in gauging the accuracy of an impairment rating can delay resource allocation. For example, cases may be improperly managed because claims adjusters, attorneys, and fact finders lack the specialized knowledge to judge the accuracy of an impairment rating. This specialized knowledge includes information such as clinical discussion pertinent to the impairment assessment process, assessment of maximal medical improvement, identification of the sections and criteria in the *Guides* that are applicable, explanation of the impairment rating process, and identification of common rating errors.

Systems aimed at improving the impairment rating process are typically targeted towards physicians. They allow physicians to input specific clinical information and they output in impairment rating based on that information; the resulting rating is erroneous if incorrect or inappropriate information is entered. Systems aimed at improving the verification of the accuracy of an impairment rating typically require review of the rating process by a third party. For example, an insurance claims department may send a questionable rating to an outside party providing expert services in reviewing the clinical data (history, physical examination findings, and diagnostic studies) and accuracy of the impairment rating. However, it is impractical to use such expert services in the initial screening of all received impairment ratings.

BRIEF SUMMARY OF EMBODIMENTS OF THE INVENTION

The present invention provides a method of verifying a permanent impairment rating for a medical diagnosis, comprising receiving a medical diagnosis of an injury and a numeric rating of permanent impairment, and comparing that numeric rating to a statistically evaluated probable impairment rating for that diagnosis. Depending on the results of the comparison, the assessed impairment rating may be reevaluated, in some cases by a trained impairment rating evaluator, and others by an expert medical staff.

According to an embodiment of the invention, a method of providing an estimated impairment rating associated with a medical diagnosis comprises receiving a diagnosis; evaluating a database of impairment rating statistics to determine a probable impairment rating corresponding to the diagnosis for the edition on the *Guides* that is applicable; and providing the probable impairment rating.

According to another embodiment of the invention, the method further comprises receiving a diagnosed maximum medical improvement value corresponding to the diagnosis; evaluating a database of maximum medical improvement values to determine a probable maximum medical improvement value resulting from the diagnosis; comparing the diagnosed maximum medical improvement value with the probable maximum medical improvement value to determine a probability of the diagnosed maximum medical improvement value; and providing the probability of the diagnosed maximum medical improvement value.

According to a further embodiment of the invention, the method further comprises determining an accuracy value of the diagnosed maximum medical improvement value if the probability of the diagnosed maximum medical improvement value meets a second predetermined condition; updating the database of maximum medical improvement values if the accuracy value of the diagnosed maximum medical improvement value meets a fourth predetermined condition; and providing the accuracy value of the diagnosed maximum medical improvement value.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE
EMBODIMENTS OF THE INVENTION

Before describing the invention in detail, it is useful to describe a few example environments with which the invention can be implemented. One such example is that of a resource allocator who must make an initial decision as to the management of a received case. In a more particular example, the resource allocator may be an insurance claims adjuster and the received case may be an insurance claim stemming from an injury. The claims adjuster (insurance, third party administrator or self-insured entity) may have received an impairment rating assessment and an assessment of the MMI date provided by a physician treating the injured party. In order to properly manage the case, the claims adjuster may desire to verify the accuracy of the impairment rating assessment and the assessment of the MMI date.

In another example, a claim adjuster may have received an incoming claim stemming from an injury in which the injured party which has not yet reached the MMI date. In such an example, the claim adjuster can more efficiently manage the claim if he is able to predict likely possible impairment rating assessments and MMI dates.

From time-to-time, the present invention is described herein in terms of these example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Figure 1:
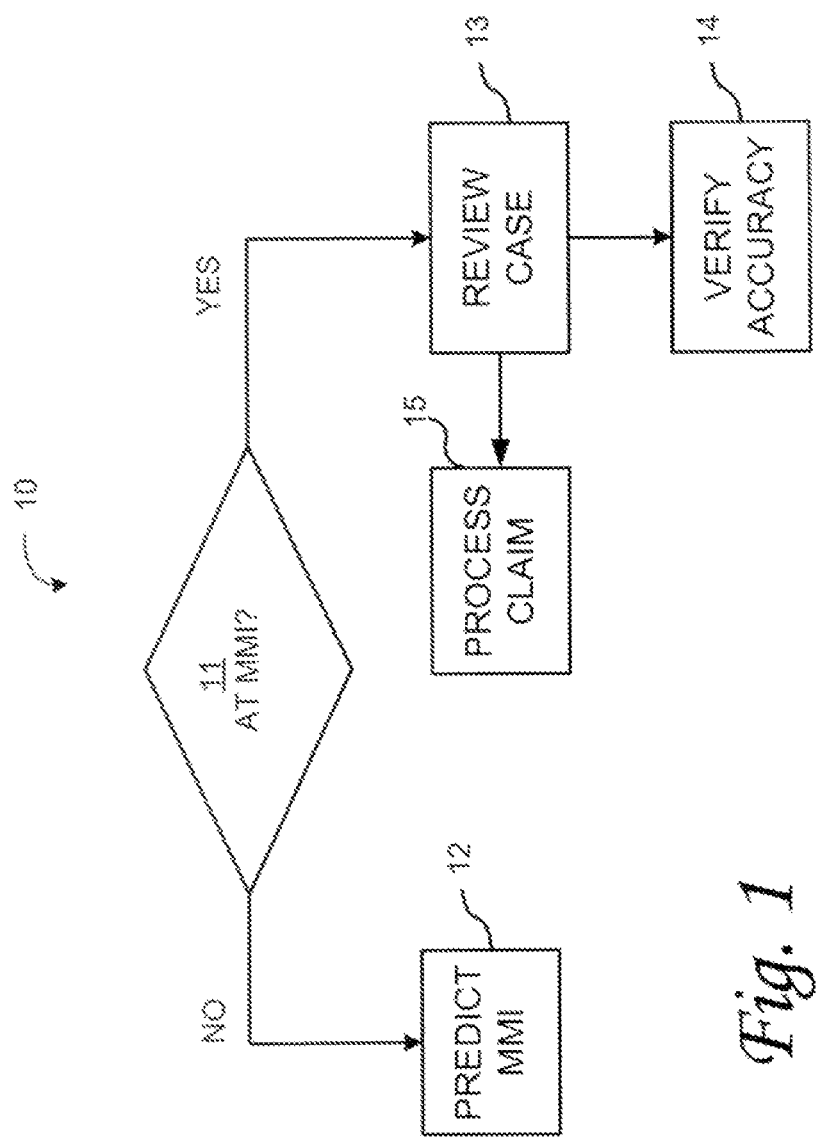
FIG. 1 illustrates a method for initial case screening according to an embodiment of the invention.

FIG. 1 illustrates a method 10 for initial case screening according to an embodiment of the invention. A stakeholder, or resource allocator, such as an insurer, third party administrator, self-insured entity, governmental organization or attorney, may receive an incoming claim for compensation and must decide or manage the disposition of the claim. In the initial case screening method 10, the stakeholder determines whether the injury that is the basis for the claim is likely at the time of maximal medical improvement (MMI) 11. In some embodiments, the likely time of MMI may be injury specific. For example, the MMI time may typically be at most twelve months for a wrist injury. In other embodiments, the likely time of MMI may be a general estimate of MMI times for all likely injury claims, such as twenty four months from injury.

In some embodiments, if the claim is not at the likely MMI time, the system may be configured to provide a predicted MMI time at step 12. For example, in a claim arising from a leg injury occurring one month before the claim, the predicted MMI time may be twelve months from injury. Accordingly, the stakeholder may delay further management of the claim until after the predicted MMI time.

In other embodiments, a claimant may have already been diagnosed and treated by a physician. That physician may have determined that the MMI date for the injury has lapsed. In this situation, if the likely MMI date for the injury has not passed, the step of predicting the MMI time 12 may further comprise determining the likely accuracy of the physician's assessment. This determination may comprise determining the likely accuracy of the physician's assessment based on that particular physician's past history of providing accurate diagnoses. Alternatively, the determination may be based on accumulated statistics and data regarding impairment values and MMIs for past claims and injuries.

If the initial case screening determines that the claim is at the likely MMI date, then the case is reviewed at step 13. The review may comprise examining the case history, the physician's assessment of the impairment rating of the injury, and the physician's previous accuracy. If the review indicates that the physician's assessment is not within an acceptable range of accuracy, then the case may be further reviewed to verify the accuracy of the physician's assessment at step 14. If the review indicates that the physician's assessment is within an acceptable range of accuracy, then the claim may move past the initial screening to the processing stage at step 15. Such a processing stage 15 may comprise determining an appropriate compensation for the claim based on an assumed accurate assessment of impairment rating. In embodiments where the method 10 further comprises verifying the accuracy of a physician's assessed MMI date, the step of case review 13 may also be completed if the physician's assessed MMI date is accurate.

Figure 2:
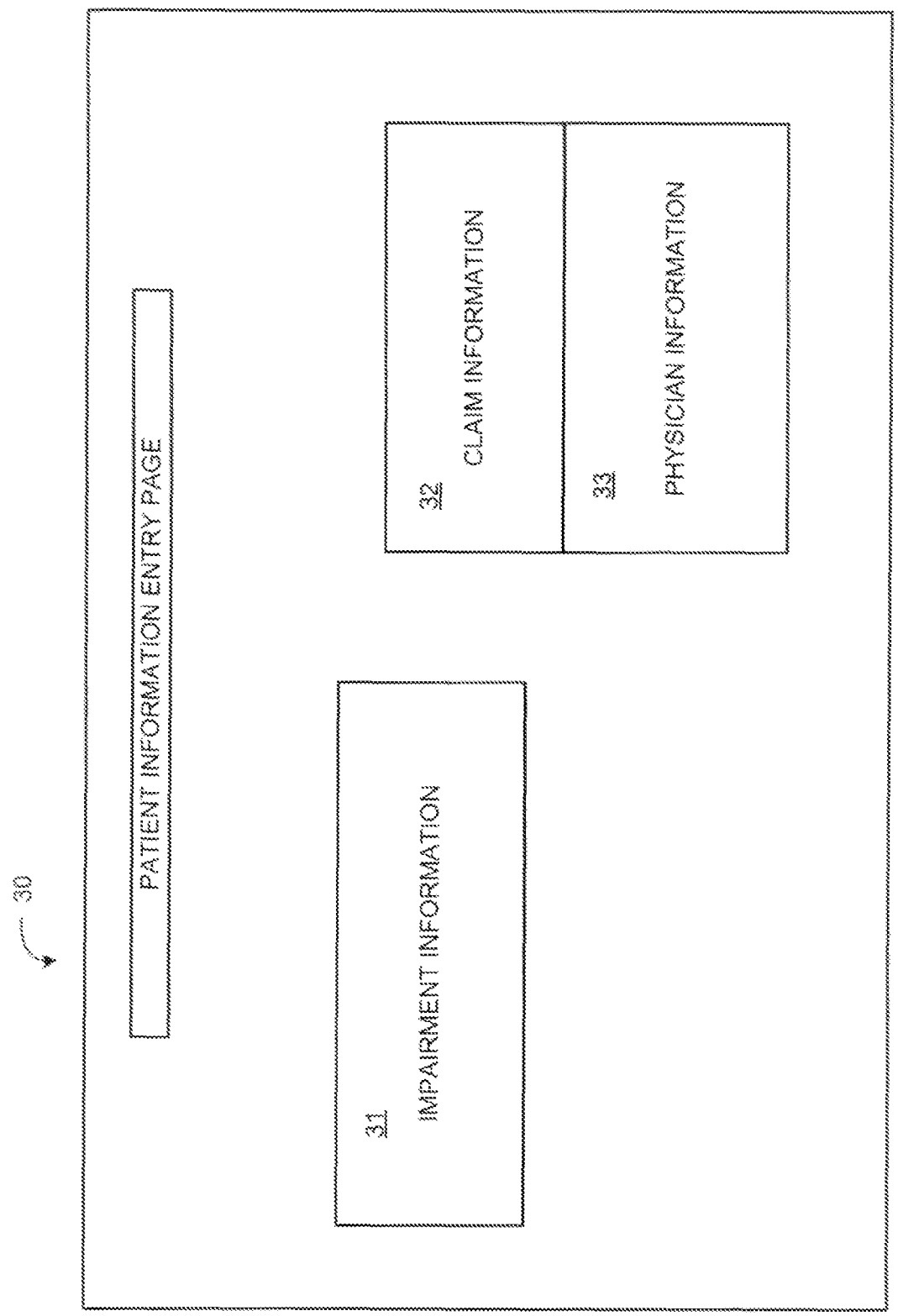
FIG. 2 illustrates a modifiable form for impairment verification according to an embodiment of the invention.

FIG. 2 illustrates a modifiable form for impairment verification according to an embodiment of the invention. Modifiable form 30 may be electronically displayed to a stakeholder or claim screener, such as in a frame of a webpage. The modifiable form 30 may comprise an impairment information field or fields 31. Impairment information field 31 may be user modifiable to input information received regarding a specific diagnosis. Such information may include the assessed impairment rating; the applicable rating units; the injury diagnosis; clinical information; and the section and edition of the impairment rating reference authority. For example, in embodiments utilizing the *AMA Guides to the Evaluation of Permanent Impairment* (the *Guides*), the input impairment information might comprise that a lower extremity injury occurred, specifically a internal derangement of the need, with an impairment rating of 20% WP, utilizing the fifth edition of the *Guides* as the rating reference.

Modifiable form 30 may further comprise a field or fields for the input of claim information 32. For example, claim information 32 may comprise a drop-down field to allow a user to select, and automatically populate the form with, information from a previous claim. The claim information 32 may also comprise fields to allow the user to input new or existing claim information manually. For example, claim information 32 may comprise fields for the claim number, the name of the claimant, a field for information on the organization managing the claim, and a field for claimant employer information. In some embodiments, claim information 32 is used to identify and keep track of the progress of claim. In further embodiments, claim information 32 may be used to collect statistics, such as impairment rating accuracy of claimants correlated to their employer. Such statistics may be used for a variety of purposes; for example, if a particular employer's employees tend to submit claims with an inaccurate impairment rating more often than is statistically likely, the system may be configured to alert the system provider or system user as to the possibility of ongoing fraud. The impairment information 31 or claims information 32 may also comprise fields for the input of the injury date, the evaluation date, and the MMI date.

Modifiable form 30 may further comprise physician information 33. For example, the modifiable form 30 may comprise a plurality of fields for inputting information about the assessing physician. Such fields might include name field, degree fields, practice locality fields, licensing information fields, or any other identifying fields. Physician information 33 may be used in case management, such as for contacting the physician. Physician information 33 may also be used in the evaluation of the accuracy of impairment assessment provided by the physician. For example, if the physician has a history of a high degree of accurate impairment assessments, the system may alert the user that the impairment assessment is provided by a reliable physician. In another example, the physician information may be used to collect data used in future evaluations of assessments provided by the physician. For example, if the physician provides an inaccurate assessment in the current claim, this data may be collected and used in the management of future claims, such as compiling a list of accurate physicians for future injury evaluations.

Further embodiments of the invention may be configured such that a user need not enter data in each field of modifiable form 30. For example, a patient's injury may be diagnosed but not yet assessed for impairment. In this scenario, a case manager may desire information regarding the impairment assessment process and the probable results thereof. Accordingly, the case manager may input only information regarding the body part or body area and the diagnosis. In other embodiments, a case manager may desire to evaluate and decide whether to use a prospective assessing physician. In these embodiments, the case manager may input information only regarding the physician's identity.

Figure 3:
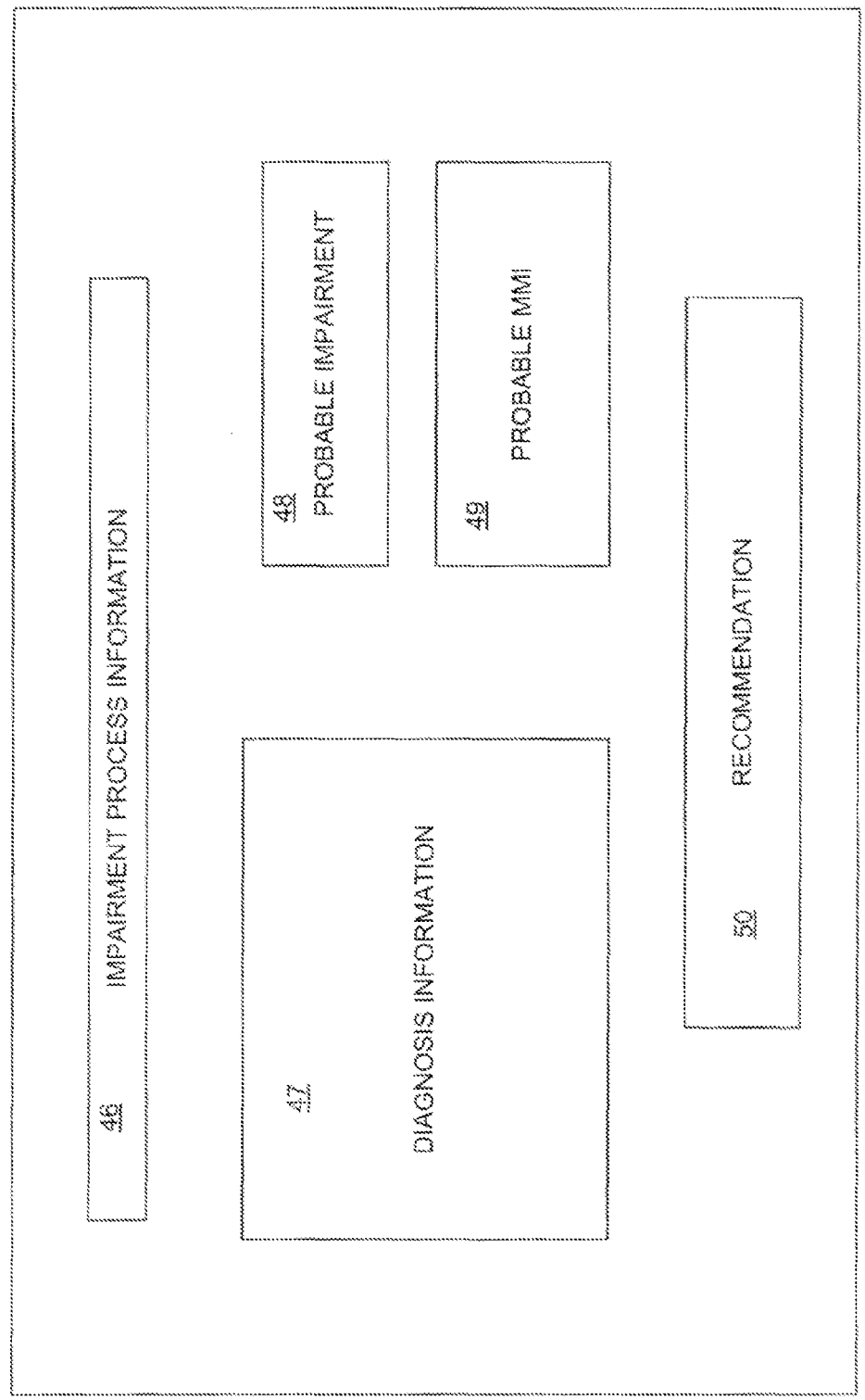
FIG. 3 illustrates the results of a request for the verification of the accuracy of impairment assessment according to an embodiment of the invention.

FIG. 3 illustrates the results of a request for the verification of the accuracy of impairment assessment according to an embodiment of the invention. Results 45 may comprise information displayed on electronic display, such as impairment rating process information 46, diagnosis information 47, information on a probable impairment rating 48, information on a probable MMI, and a recommendation 50 for further action. Impairment rating process information 46 might comprise information regarding the assessment process suggested by the assessment rating reference text. For example, impairment process information 46 might comprise a description of the chapter and methods for impairment rating used by the assessment rating reference text. In a lower extremity (leg) injury processed using the fifth edition of the *Guides*, information 46 might describe common approaches for determining impairment of the lower extremity, such as muscle atrophy, muscle strength, range of motion or by diagnosis. This information might also include any applicable tables, charts, or graphs to illustrate the impairment rating process. Impairment rating process information 46 might also comprise information regarding common sources of error in the assessment rating process. This information may be helpful for case review in identifying the potential source of an inaccurate assessment rating.

Diagnosis information 47 might comprise information describing the diagnosis included in a modifiable form, such as the one described in FIG. 2. For example, diagnosis information 47 might comprise information regarding common injuries and the injured body portion, and information regarding the specific injury. For example an internal derangement of the knee, the information may comprise a description of the applicable parts of the knee that are injured in derangements, and a description of which parts are most often injured. This information may be useful in allowing a non-expert case screener to manage the claim.

Probable impairment information 48 might comprise information regarding common impairment rating stemming from the injury at issue. For example, if the injury is an internal knee derangement and the impairment rating assessment reference is the fifth edition of the *Guides*, probable impairment information 48 might comprise a report that the most common expert average rating is 4.3% WP. The values of the expert rating are derived from the review of permanent impairment rating reports by experts and collection of that information in databases. Probable impairment information 48 might also comprise a comparison of the most common expert average rating with the actual reported rating. For example, if the reported rating was 20% WP, impairment information 48 might comprise information regarding this discrepancy and potential sources. For example, impairment information 48 might inform the user that the reported rating is likely inaccurate. Impairment information 48 might also inform the user that if 20% WP is an accurate rating, then a specific type of knee derangement is the likely injury. This may inform the user and assist in case management; for example, a specific type of knee derangement may have a later MMI date.

Probable MMI information 49 might comprise information such as an average expert rated MMI date, and information regarding the progression of the injury. Probable MMI information 49 might also include a comparison between the reported MMI date and the probable MMI date. This information may be useful in assisting the case manager to determine if a reevaluation is necessary at a later time, for example if the probable MMI date is much later than the reported MMI date. Probable MMI information 49 may also provide a prognosis of future impairment based on the date of the injury and the time remaining until the probable MMI date. For example, using databases and data collection methods as described herein, impairment statistics regarding ratings made before the MMI date may be collected. Although impairment is typically defined as permanent impairment arising after the MMI date, the statistics may nevertheless be useful in prediction.

Results 45 may further comprise a recommendation 50. Recommendation 50 may be based on a comparison between the reported impairment rating and the average expert reported rating. Recommendation 50 might also be based on an assessment of the rating physician's previous accuracy. Recommendation 50 might further be based on various statistical methods to determine the likely accuracy of the average expert reported rating. For example, the recommendation may use a Bayesian type analysis to determine the probable accuracy of the assessed impairment rating conditionally dependent on a variety of possible specific injuries included within the general diagnosis and/or historical information on the reliability of that physician's ratings. Recommendation 50 might also be based on the degree of likely inaccuracy of the impairment assessment. For example, if the impairment assessment is likely very inaccurate, the recommendation 50 might comprise recommending that the claim be reviewed by an expert reviewer, such as a physician. In contrast, if the impairment assessment is within acceptable bounds of likelihood, recommendation 50 might comprise recommending that the claim be re-reviewed by an internal review process, without requiring an expert review. In further embodiments, this recommendation might be provided in a visually alerting method. For example, a bright red box may appear to indicate a highly suspicious impairment assessment.

In further embodiments, recommendation 50 may be based upon the deviation from the assessed impairment rating and a probable impairment rating. For example, if a probable impairment rating is 5% WP and the assessed impairment rating is 45% WP, then the recommendation 50 may report the 40% WP deviation. In these embodiments, basing recommendation 15 on deviation from probable impairment rating may serve a twofold purpose. First, the amount of deviation may serve as an indication of the probability of inaccurate assessment, where a greater deviation indicates a greater probability of inaccurate assessment. Second, the amount of deviation may serve as an indication of probable cost of correcting the inaccurate assessment. For example, given limited allocation resources, a 5% WP deviation between the reported assessment and the probable assessment may not be worth the expense of re-examining the case, despite the inaccuracy of the assessment.

In further embodiments, additional information may be displayed with the results 45. For example, information regarding the assessing physician might be displayed, such as the physician's history of accuracy and a secondary recommendation based on the history of accuracy. For example, if the assessing physician has a long history of providing an accurate rating, a secondary recommendation might be provided to re-review the case, even if the assessment is within normally acceptable bounds. Other information might include a detailed claim or file history describing the injured parties known history of injuries, and information or links to information regarding the specific injury or accident at issue.

Further embodiments of the invention may be configured such that the results 45 are conditioned upon the information received by a user. For example, where a claimant's injury has been diagnosed but not yet assessed for impairment, the user may have included only information regarding the diagnosis. In this example, results 45 may comprise only impairment process information 46. In an example where a user desires information regarding a prospective assessing physician, recommendation 50 may comprise information on the physician's accuracy. If the user also input information regarding the claimant's diagnosis, recommendation 50 may comprise information on the physician's accuracy with regard to the specific diagnosis.

Figure 4:
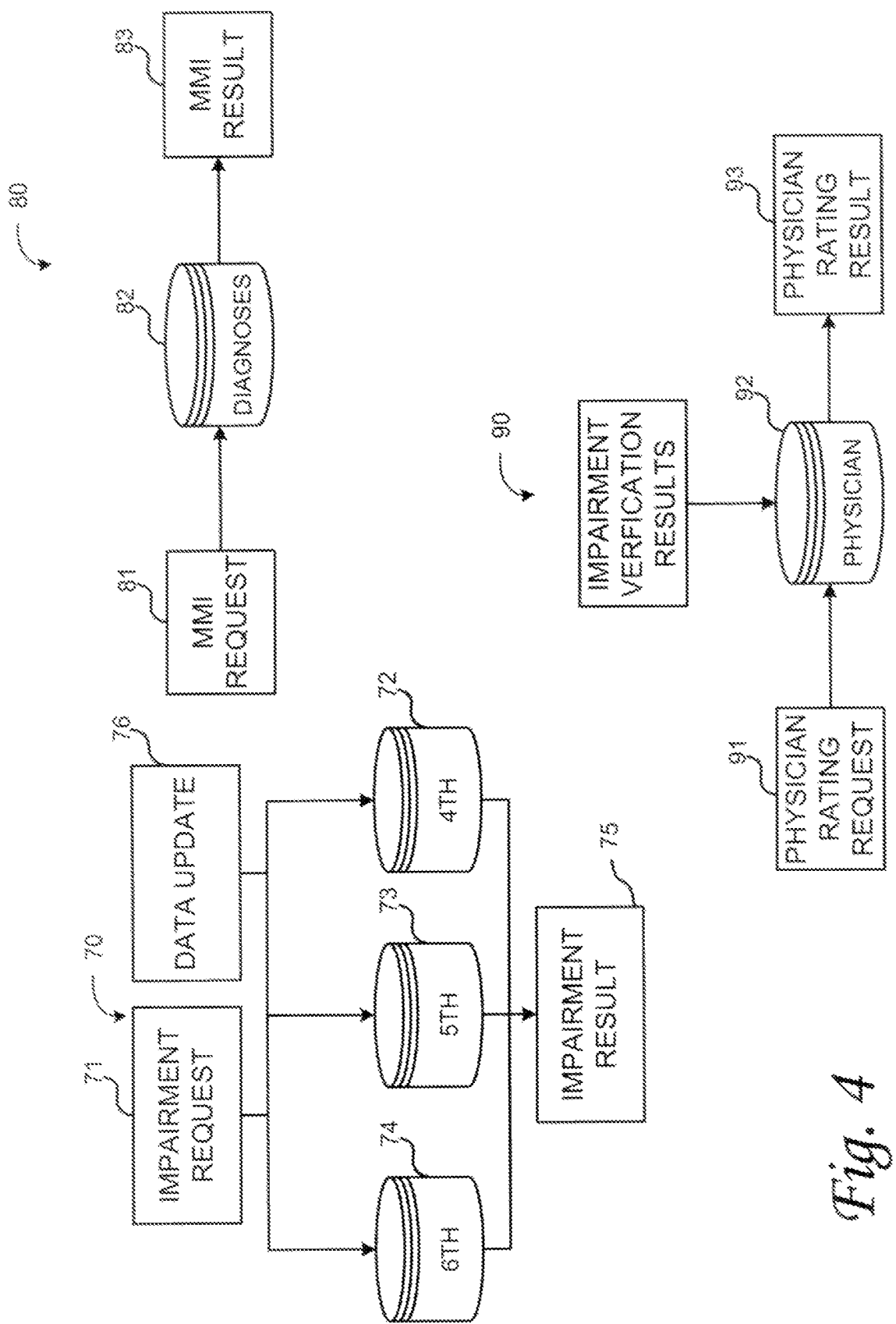
FIG. 4 illustrates a variety of relational databases and uses thereof according to an embodiment of the invention.

FIG. 4 illustrates a variety of relational databases and uses thereof according to an embodiment of the invention. Impairment database system 70 may comprise a database or databases of compiled statistics of previously made accurate impairment assessments of various injuries. For example, the compiled results of a plurality of accurate impairment evaluations can be used to estimate the accuracy of a newly provided impairment evaluation. The database or databases of compiled statistics may further comprise information regarding the impairment process for the various injuries according to the compatible reference texts. These databases may be configured to return a variety of information based on provided queries. For example, the databases may be configured to return a probable impairment rating for a specific injury diagnosis. This information may be used to determine, for example, the deviation from an assessed impairment rating and the probable impairment rating for use in further case management. Impairment database system 70 may comprise a system 71 for querying a database, or plurality of databases 74, 73, and 72, and a system 75 for returning the result of the query. As different impairment evaluation reference texts may use different systems of evaluation, different databases may be provided for the various compatible reference texts. For example, databases 74, 73, and 72 may comprise information and statistics regarding assessments made using the fourth, fifth, and sixth editions of the *Guides*. In some embodiments, system 71 for querying the databases may comprise an automatic database querying system that generates an appropriate query based on information input by a system user. For example, if a case manager requested a verification of an assessment made using the procedures outlined in the fourth edition of the *Guides*, system 71 may generate an appropriate query for database 72.

In some embodiments, the impairment rating statistics databases may be organized on the basis of evaluation. For example, databases 72, 73, and 74 may be organized according to a specific edition of an impairment assessment reference text. Further embodiments may provide additional databases of statistics regarding other impairment assessment reference text. For example, additional databases may be provided that comprise information regarding statistics on systems and impairment rating such as those used in non-AMA compliant jurisdictions, such as New York, Florida, Utah, and Wisconsin. Other embodiments may provide databases regarding statistics of other disability-type information. For example, databases may be compiled regarding statistics of accurate permanent disability ratings, such as those used in the California Permanent Disability Rating Schedule.

Additional embodiments may organize the compiled data in other manners. For example, in the transitions between the fourth, fifth, and sixth editions of the *Guides*, the method of assessing the impairment resulting from some injuries remain constant. Accordingly, if the method of assessing impairment has not changed between editions, then statistics of accurate assessments made under an earlier edition may be validly applied to assessments made under a later edition. In these embodiments, a database of accurate impairment assessments may be compiled and organized by diagnosis rather than by reference text. This database organized by diagnosis may, for example, comprise an array of statistics regarding the assessment of injuries whose method of impairment assessment has not varied, and an array of references to edition specific arrays of statistics regarding the assessment of injuries whose method of impairment assessment has varied.

System 75 may be configured to return the result of a query provided by the system 71. For example, if query system 71 provided each database 74, 73, and 72 a general request to return information regarding the probable results of the impairment assessment of the specific injury, such as a knee derangement, impairment result system 75 may return information regarding the probable impairment rating result under each assessment reference text, and information regarding the impairment assessment process for these reference texts.

Other embodiments may utilize systems of databases that contain segregated information. For example, a first system of databases may comprise statistics regarding previous accurate assessments of impairments stemming from various injuries, while a second system of databases may comprise information regarding the impairment assessment process used by the various impairment assessment references. In these embodiments, impairment request system 71 may be configured to generate and provide requests to both systems of databases, and impairment result system 75 may be configured to receive results from both systems of databases and format these results for presentation to the user.

Further embodiments may provide methods and systems 76 for updating and adding statistics to the databases. As additional accurate impairment assessment statistics are developed, such as through expert re-reviews of identified inaccurate impairment assessments, data update system 76 may update databases 72, 73, and 74 with these new statistics. In additional embodiments, other impairment assessment results might be included and added into the databases. For example, if a physician having a known high degree of accuracy provides an impairment assessment that agrees with the statistically predicted impairment, then this data point may be included in the appropriate database, thereby increasing the statistical weight of that predicted impairment.

Further embodiments may involve the conversion of a permanent impairment rating into a permanent disability rating such as those based on protocols and procedures for a jurisdiction, such as the State of California Permanent Disability Rating Schedule, and systems 76 for updating and adding statistics to the databases. In additional embodiments, other assessment results might be included and added into the databases.

MMI database system 80 may comprise a database 82 of statistics on MMI dates for a plurality of diagnoses. In some embodiments, the date of maximum medical improvement does not vary according to which impairment assessment reference text is employed. Accordingly, MMI database 82 might not be segregated according to reference text. In other embodiments, database 82 may comprise statistics regarding other relevant dates. For example, in an embodiment employed to verify assessments under the California Permanent Disability Rating Schedule, database 82 may comprise statistics regarding the translation of permanent impairment ratings into permanent disability ratings; including, for example, information on Future Earning Capacity adjustments, occupational information, and age adjustments. Further embodiments may include other information in database 82, such as information regarding relevant factors that influence the MMI date. Alternative embodiments may include this information in other external databases.

MMI system 81 may be configured to generate a query for the database 82 in accordance with a request for information provided by a system user, such as a request for information regarding the probable MMI date for the injury. In embodiments where the database 82 also comprise information regarding information on MMI assessment, MMI request system 81 may be further configured to generate a query requesting information regarding the injury to be screened. Alternatively, in embodiments where this information is maintained in an external database, MMI request system 81 may be configured to connect and provide an appropriate request for information to this external database.

MMI result 83 may be provided directly to a user in response to information. For example, MMI result 83 may be presented via a separable frame of a results page, as described herein. Alternatively, MMI result 83 may be provided to other systems or subsystems for further formatting before presentation to a user. For example, MMI result 83 may be compared to an input MMI, and the results of the comparison may be presented to the user.

Further embodiments may provide alternative methods and systems for updating database 82. For example, a system may be implemented that automatically requests information about injury progression of a claimant at a predetermined time, such as a request for injury history two years after the date of case resolution. Accordingly, through these methods and systems the accuracy of database 82 may be improved.

Physician assessment database system 90 may be configured to provide statistical information regarding impairment assessing physicians' accuracies. Database 92 may contain information regarding statistics on various physicians' abilities to accurately assess impairments. Such statistics might include a physician's general accuracy at impairment ratings, a physician's specific accuracy at impairment rating for particular body regions or diagnoses, and other physician performance information such as the overall average of the physician's ratings compared to the overall average projected for that specific diagnosis. Such information may be used for a variety of purposes. For example, if a physician displays a high degree of precision, but a low degree of accuracy this may indicate that the physician has performs a specific error propagating through all of the physician's ratings. Accordingly, the physician could be trained or informed of this error, thereby improving his accuracy. As another example, a physician may have a relatively low degree of accuracy with a specific body portion, or under a specific assessment rating system, and may therefore be provided with additional training regarding that specific body region or rating system. This information may also be used by a system user in a variety of physician selection tasks. For example, a physician with a high degree of accuracy may be included on a list of insurer approved impairment raters, or may be invited to participate as an expert in a claim review process.

Physician rating request system 91 may be configured to query the physician database 92 in a manner similar to the other query systems described herein. Similarly, physician rating result 93 may be presented or formatted similarly to the other results described herein. For example, physician rating result 93 may comprise a general assessment of the physician's accuracy, such as through a numerical accuracy value. As another example, physician rating result 93 may comprise a spreadsheet information regarding the physician's previous impairment assessments and their accuracies.

Figure 5:
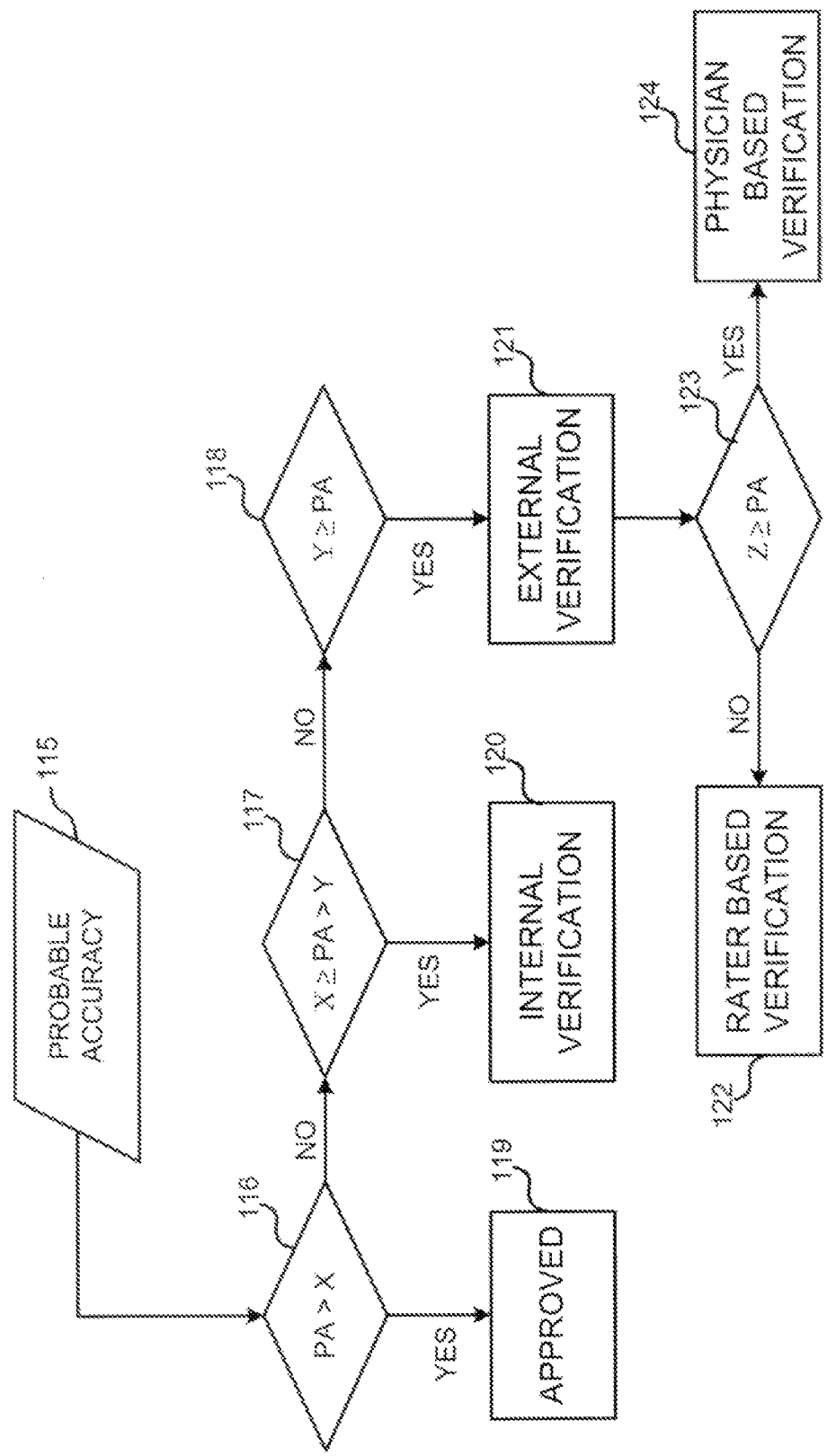
FIG. 5 illustrates a method of case management according to an embodiment of the invention.

FIG. 5 illustrates a method of case management according to an embodiment of the invention. In this embodiment a case manager improve the results of a physician's impairment assessment regarding an injury and has received a report on the probable accuracy of the received impairment assessment, as described herein. The case manager may desire to manage the case differently based on the likelihood that the impairment assessment is accurate. For example, various options for further case management might comprise submitting the case to an approval department, internally verifying the claim's impairment process, or submitting the case to an external verification system.

In this embodiment, the received probable accuracy of the physician's assessments 115 is examined to determine further case management steps. If the probability that the impairment was accurate meets a first precondition 116, then case management 119 may comprise approving the case, or allowing the case to proceed to a less rigorous review process. For example, if the probability of accurate assessment is greater than 95%, then the case may be transferred to an approval system for injury compensation.

If the probability of accurate assessment does not meet first condition 116 but does meet a second condition 117, then the case may be submitted to an internal verification system 120. For example, if the an accurate assessment is less than 95%, but greater than 75%, then the case may be re-reviewed by an internal assessment reviewer. In some embodiments, the internal review may comprise a multi-structured internal review process. For example, a company may have a assessment expert, such as a physician, and an experienced assessment rater who is not a qualified expert. In these embodiments, the case may be managed differently based on the probability of accurate assessment. For example, assessments with probabilities greater than 85% may be dealt with by the assessment expert, while assessments with probabilities between 85% and 75% may be dealt with by the experienced assessment rater.

In some embodiments, if the probability of accuracy does not meet a third condition 118, in the case may be transferred to an external verification system 121. Such an external verification system 121 may comprise a staff of experts who will physically reviewed the reports, critique the reports, and prepared for the reports describing the findings. In further embodiments, the method of review by the external verification system 121 may be based upon a fourth condition 123. For example, if the probability of accuracy is greater than 50% then the case may be managed by a trained assessment rater, while this the probability of accuracy is less than 50% in the case may be managed by one or more assessment experts such as physicians.

Further embodiments may base case management decisions on additional metrics or relevant measurements. For example, in embodiments measuring the deviation between a probable impairment rating and an actual assessed impairment rating, case management may be based on these deviations. In these embodiments, the conditions 116, 117, 118, and 123 might be various comparisons of an impairment deviation in relation to certain preconditions. For example, the case may be approved 119, if the deviation from probable impairment is less than a predetermined number, such as 4.3%. The case may be handled internally 120, if the deviation is within a predetermined range, such as between 4.3% and 8.2%. The case may be handled externally 121, if the deviation is outside this predetermined range. In further embodiments, the external verification 121 may comprise rater-based verification 122, or physician-based verification 124, depending on the deviation. For example, the case may be presented to a trained expert rater if the deviation is less than 20%, while the case may be presented to a trained physician, or group of physicians, if the deviation is greater than 20%. In these embodiments, a limited amount of resources may be allocated in a cost-effective manner. External verification by a group of physicians will likely cost more resources than internal verification. Accordingly, verification by the group of physicians only takes place if the deviation indicates that the cost of evaluation is less than the difference between the cost of paying an accurate claim and paying the inaccurate claim.

Still further embodiments may take into consideration a combination of multiple measurements. For example, the case management decisions may be made based on the deviation, the probability of inaccurate assessment, and the assessing physician's history of accurate assessment. For example, an expectation value of cost may be determined according to the probability of inaccurate assessment and the physician's history of accurate assessment. Potential cost savings may be computed using the deviation and be compared to this expectation value.

In some embodiments, the impairment assessment verification described herein as external may take place within a user's organization. For example, a user may employ a variety of assessment verifiers covering a range of depth of investigation. A user might employ an initial verifier to review cases with small amounts of deviation from expected impairment assessment; a secondary verifier to review cases with moderate deviations, and a tertiary verifier to review cases with large deviations. Such reviewers may fill the roles described herein as internal or external. For example, the tertiary the verifier may comprise a physician, or group of physicians, employed by a large user organization to investigate abnormally large deviations from expected impairment ratings.

Figure 6:
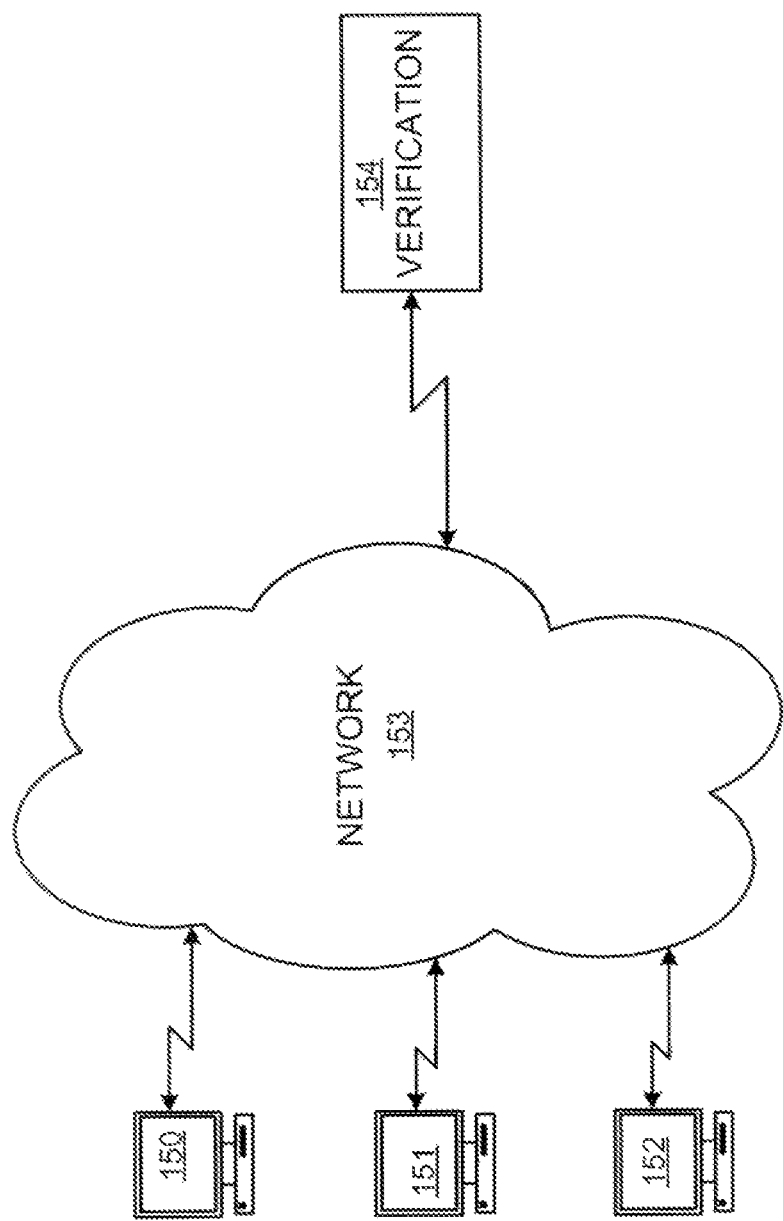
FIG. 6 illustrates an example system for providing impairment rating verification according to an embodiment of the invention.

FIG. 6 illustrates an example system for providing impairment rating verification according to an embodiment of the invention. A plurality of user devices 150, 151, and 152 may be configured to communicate with a verification system 154 via a network 153. User devices 150, 151, and 152 may be configured to provide information to and receive results from verification system 154 regarding impairment assessments, as described herein. For example, a computer program product may be embodied on a computer readable medium contained within user device 150 that is configured to receive information, such as through a modifiable form, and transmit that information via network 153 to verification system 154. Verification system 154 may be configured to return appropriate results according to the received information, as described herein. User device 151 may be configured to provide information to verification system 154 in other manners, such as through a webpage hosted by a server contained within network 153, or hosted by a server contained within verification system 154. In such an embodiment, verification system 154 may also use a webpage to return the requested information to user device 151, as described herein. In other embodiments, the results might be transmitted to a user of the device 151 in other manners, such as through e-mail, a telephone call, or a letter.

Figure 7:
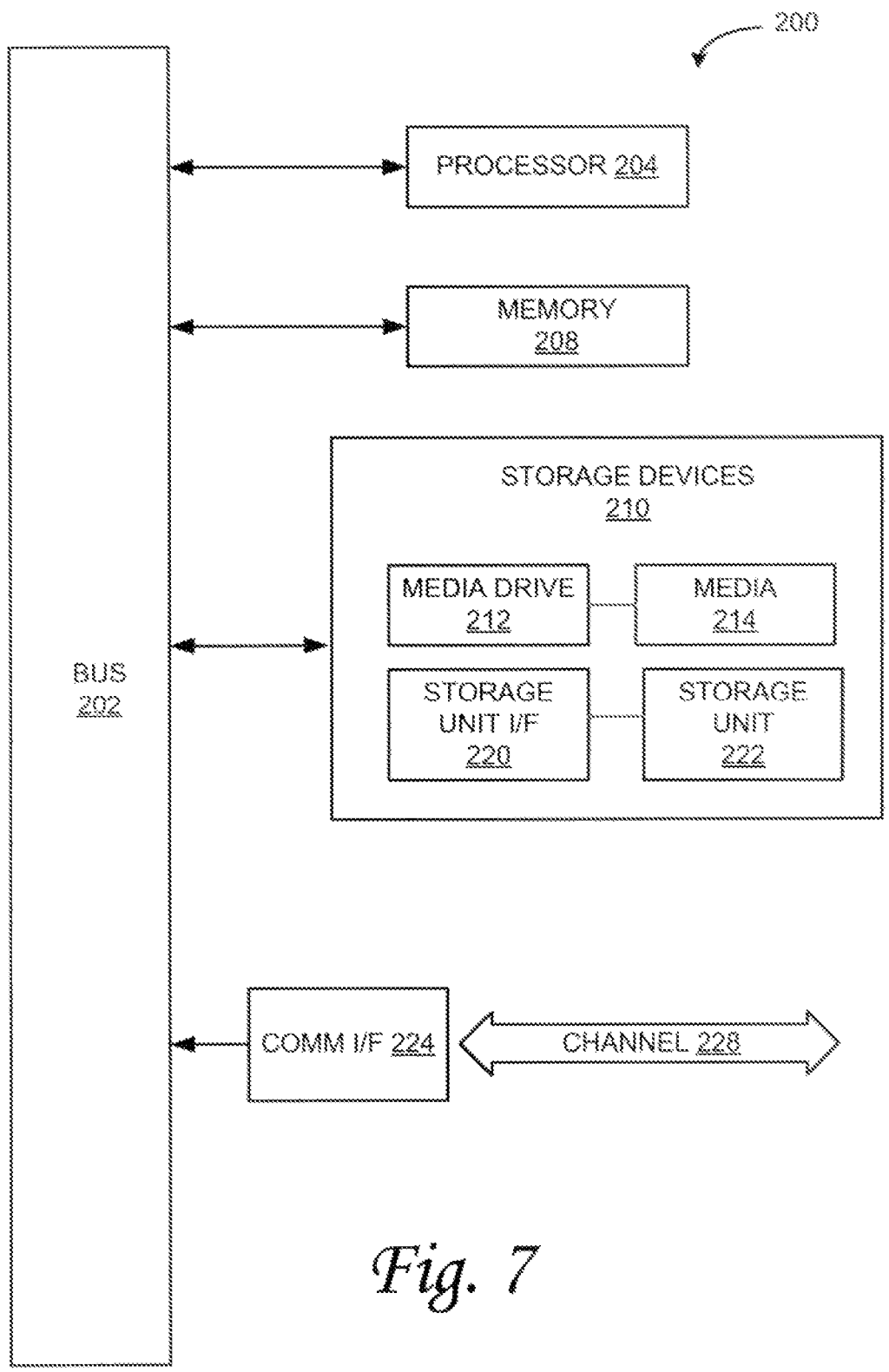
FIG. 7 illustrates a computing module that may be utilized to implement various aspects of embodiments of the invention.

As used herein, the term module might describe a given unit of functionality that can be performed in accordance with one or more embodiments of the present invention. As used herein, a module might be implemented utilizing any form of hardware, software, or a combination thereof. For example, one or more processors, controllers, ASICs, PLAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the invention are implemented in whole or in part using software, in one embodiment, these software elements can be implemented to operate with a computing or processing module capable of carrying out the functionality described with respect thereto. One such example-computing module is shown in FIG. 7. Various embodiments are described in terms of this example-computing module 200. After reading this description, it will become apparent to a person skilled in the relevant art how to implement the invention using other computing modules or architectures.

Referring now to FIG. 7, computing module 200 may represent, for example, computing or processing capabilities found within desktop, laptop and notebook computers; handheld computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 200 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 200 might include, for example, one or more processors, controllers, control modules, or other processing devices, such as a processor 204. Processor 204 might be implemented using a general-purpose or special-purpose processing engine such as, for example, a microprocessor, controller, or other control logic. In the example illustrated in FIG. 7, processor 204 is connected to a bus 202, although any communication medium can be used to facilitate interaction with other components of computing module 200 or to communicate externally.

Computing module 200 might also include one or more memory modules, simply referred to herein as main memory 208. For example, preferably random access memory (RAM) or other dynamic memory, might be used for storing information and instructions to be executed by processor 204. Main memory 208 might also be used for storing temporary variables or other intermediate information during execution of instructions to be executed by processor 204. Computing module 200 might likewise include a read only memory ("ROM") or other static storage device coupled to bus 202 for storing static information and instructions for processor 204.

The computing module 200 might also include one or more various forms of information storage mechanism 210, which might include, for example, a media drive 212 and a storage unit interface 220. The media drive 212 might include a drive or other mechanism to support fixed or removable storage media 214. For example, a hard disk drive, a floppy disk drive, a magnetic tape drive, an optical disk drive, a CD or DVD drive (R or RW), or other removable or fixed media drive might be provided. Accordingly, storage media 214, might include, for example, a hard disk, a floppy disk, magnetic tape, cartridge, optical disk, a CD or DVD, or other fixed or removable medium that is read by, written to or accessed by media drive 212. As these examples illustrate, the storage media 214 can include a computer usable storage medium having stored therein computer software or data.

In alternative embodiments, information storage mechanism 210 might include other similar instrumentalities for allowing computer programs or other instructions or data to be loaded into computing module 200. Such instrumentalities might include, for example, a fixed or removable storage unit 222 and an interface 220. Examples of such storage units 222 and interfaces 220 can include a program cartridge and cartridge interface, a removable memory (for example, a flash memory or other removable memory module) and memory slot, a PCMCIA slot and card, and other fixed or removable storage units 222 and interfaces 220 that allow software and data to be transferred from the storage unit 222 to computing module 200.

Computing module 200 might also include a communications interface 224. Communications interface 224 might be used to allow software and data to be transferred between computing module 200 and external devices. Examples of communications interface 224 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 224 might typically be carried on signals, which can be electronic, electromagnetic (which includes optical) or other signals capable of being exchanged by a given communications interface 224. These signals might be provided to communications interface 224 via a channel 228. This channel 228 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 208, storage unit 220, media 214, and signals on channel 228. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 200 to perform features or functions of the present invention as discussed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the term "physician" is used to describe the individual who may provide a rating and this may include an allopathic physician, osteopathic physician, chiropractor, psychologist, podiatrist, physical therapist, occupational therapist, or others who provide impairment ratings; the term "claims adjuster" is used to describe the individual responsible for managing a claim and this may be in a variety of setting, including but not limited to insurance company, third party administration organization, self-insured organization, governmental agency, or legal organization; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. Computer executable program code embodied on a non-transitory computer readable medium configured to perform the functions of:

receiving a diagnosis;
evaluating a database of impairment rating statistics to determine a probable impairment rating resulting from the diagnosis; providing the probable impairment rating;
receiving an assessed impairment rating corresponding to the diagnosis;
comparing the assessed impairment rating and the probable impairment rating to determine a probability that the assessed impairment rating is inaccurate; and providing the probability.

2. The computer executable program code of claim 1, further configured to perform the functions of:
determining a deviation of the assessed impairment rating from the probable impairment rating; and
providing the deviation.

3. The computer executable program code of claim 2, further configured to perform the functions of:
determining a physician accuracy rating using the probability of previously assessed impairment ratings; and
providing the physician accuracy rating.

4. The computer executable program code of claim 2, further configured to perform the function of updating the database using the assessed impairment rating if the probability meets a predetermined condition.

5. The computer executable program code of claim 1, further configured to perform the function of providing information regarding clinical information of the diagnosis, or impairment assessment information of the diagnosis.

6. The computer executable program code of claim 1, further configured to perform the functions of:
receiving a diagnosed maximum medical improvement value corresponding to the diagnosis;
evaluating a database of maximum medical improvement values to determine a probable maximum medical improvement value resulting from the diagnosis;
comparing the diagnosed maximum medical improvement value with the probable maximum medical improvement value to determine a probability that the diagnosed maximum medical improvement value is inaccurate; and
providing the probability of the diagnosed maximum medical improvement value.

7. The computer executable program code of claim 6, further configured to perform the functions of:
determining an accuracy value of the diagnosed maximum medical improvement value if the probability of the diagnosed maximum medical improvement value meets a third predetermined condition;
updating the database of maximum medical improvement values if the accuracy value of the diagnosed maximum medical improvement value meets a fourth predetermined condition; and
providing the accuracy value of the diagnosed maximum medical improvement value.

8. A system for accurate patient diagnosis, comprising:
a form configured to be displayed to a user and to receive a diagnosis;
a database comprising impairment rating statistics;
a computer program embodied on a computer readable medium configured to return a probable impairment rating corresponding to the diagnosis; and
a result configured to be displayed to the user and comprising the probable impairment rating;
wherein the form is further configured to receive an assessed impairment rating of the diagnosis;
wherein the computer program is further configured to compare the assessed impairment rating and the probable impairment rating to determine a probability that the assessed impairment rating is inaccurate.

9. The system of claim 8, wherein:
the form is further configured to receive the assessed impairment rating of the diagnosis;
the computer program is further configured to determine a deviation between the probable impairment rating and received impairment rating; and
the result further comprises the deviation.

10. The system of claim 9, wherein the computer program is further configured to provide a recommendation to verify the accuracy of the assessed impairment rating if the deviation meets a first predetermined condition.

11. The system of claim 9, wherein:
the form is further configured to receive a diagnosed maximum medical improvement value of the diagnosis;
the database further comprises maximum medical improvement value statistics;
the computer program is further configured to return a probable maximum medical improvement value corresponding to the diagnosis;
the computer program is further configured to determine a likelihood of the diagnosed maximum medical improvement value; and
the result further comprises the probable maximum medical improvement value and the likelihood of the diagnosed maximum medical improvement value.

12. Computer executable program code embodied on a non-transitory computer readable medium configured to perform the functions of:
receiving a diagnosis;
evaluating a database of impairment rating statistics to determine a probable impairment rating resulting from the diagnosis;
providing the probable impairment rating;
receiving an assessed impairment rating corresponding to the diagnosis;
comparing the assessed impairment rating and the probable impairment rating to determine a probability that the assessed impairment rating is inaccurate; and
providing the probability.

13. The computer executable program code of claim 12, further configured to perform the functions of:
determining a physician accuracy rating using the probability of previously assessed impairment ratings; and
providing the physician accuracy rating.

14. The computer executable program code of claim 12, further configured to perform the function of updating the database using the assessed impairment rating if the probability meets a predetermined condition.

15. The computer executable program code of claim 12, further configured to perform the function of providing information regarding clinical information of the diagnosis, or impairment assessment information of the diagnosis.

16. The computer executable program code of claim 13, further configured to perform the functions of:
receiving a diagnosed maximum medical improvement value corresponding to the diagnosis;
evaluating a database of maximum medical improvement values to determine a probable maximum medical improvement value resulting from the diagnosis;
comparing the diagnosed maximum medical improvement value with the probable maximum medical improvement value to determine a probability that the diagnosed maximum medical improvement value is accurate; and
providing the probability of the diagnosed maximum medical improvement value.

17. The computer executable program code of claim 16, further configured to perform the functions of:
determining an accuracy value of the diagnosed maximum medical improvement value if the probability of the diagnosed maximum medical improvement value meets a third predetermined condition;
updating the database of maximum medical improvement values if the accuracy value of the diagnosed maximum medical improvement value meets a fourth predetermined condition; and
providing the accuracy value of the diagnosed maximum medical improvement value.

* * * * *

UNITED STATES PATENT AND TRADEMARK OFFICE
CERTIFICATE OF CORRECTION

PATENT NO. : 8,615,411 B2  Page 1 of 1
APPLICATION NO. : 13/478022
DATED : December 24, 2013
INVENTOR(S) : Christopher Roy Brigham It is certified that error appears in the above-identified patent and that said Letters Patent is hereby corrected as shown below:

Title page, item [12] and item [76] Inventor: "Bingham" should read --Brigham--

Signed and Sealed this
Twenty-first Day of April, 2015

Michelle K. Lee
*Director of the United States Patent and Trademark Office*